US012767662B2

(12) United States Patent
Zhang et al.

(10) Patent No.: US 12,767,662 B2
(45) Date of Patent: *Oct. 20, 2026

(54) CRYSTAL FORM OF PYRROLOPYRIMIDINE COMPOUND AND PREPARATION METHOD FOR CRYSTAL FORM

(71) Applicant: ZHEJIANG LONGCHARM BIO-TECH PHARMA. CO., LTD., Zhejiang (CN)

(72) Inventors: Yang Zhang, Shanghai (CN); Wentao Wu, Shanghai (CN); Kaijun Geng, Shanghai (CN)

(73) Assignee: ZHEJIANG LONGCHARM BIO-TECH PHARMA. CO., LTD., Zhejiang (CN)

(*) Notice: Subject to any disclaimer, the term of this patent is extended or adjusted under 35 U.S.C. 154(b) by 345 days.

This patent is subject to a terminal disclaimer.

(21) Appl. No.: 18/559,679

(22) PCT Filed: May 10, 2022

(86) PCT No.: PCT/CN2022/092059

§ 371 (c)(1),
(2) Date: Nov. 8, 2023

(87) PCT Pub. No.: WO2022/237808

PCT Pub. Date: Nov. 17, 2022

(65) Prior Publication Data

US 2024/0239802 A1 Jul. 18, 2024

(30) Foreign Application Priority Data

May 12, 2021 (CN) ......................... 202110518999.9

(51) Int. Cl.

*C07D 487/04* (2006.01)
*A61K 31/519* (2006.01)
*A61P 35/02* (2006.01)

(52) U.S. Cl.

CPC .......... *C07D 487/04* (2013.01); *A61K 31/519* (2013.01); *A61P 35/02* (2018.01)

(58) Field of Classification Search

CPC ...... C07D 487/04; A61P 35/02; A61K 31/519
See application file for complete search history.

(56) References Cited

U.S. PATENT DOCUMENTS

| | | | | |
|---|---|---|---|---|
| 4,432,987 A * | 2/1984 | Barth | ...................... | A61P 31/04 514/193 |
| 12,378,253 B2 * | 8/2025 | Zhang | ...................... | A61P 37/02 |
| 2017/0182053 A1 * | 6/2017 | Lapierre | .............. | A61K 31/519 |
| 2023/0357248 A1 * | 11/2023 | Zhang | ...................... | A61P 37/02 |

FOREIGN PATENT DOCUMENTS

| | | |
|---|---|---|
| CN | 109890821 | 6/2019 |
| CN | 112608318 | 4/2021 |
| CN | 108699062 | 10/2021 |
| JP | 7473642 | 4/2024 |
| WO | WO 2020/036913 | 2/2020 |
| WO | WO 2021/093839 | 5/2021 |

OTHER PUBLICATIONS

S. Morissette, et al. Advanced Drug Delivery Reviews, vol. 56, Issue 3, 2004, pp. 275-300. (Year: 2004).*
International Search Report issued in corresponding PCT Application No. PCT/CN2022/092059, mailed Aug. 11, 2022. (English Translation Provided).

* cited by examiner

*Primary Examiner* — James H Alstrum-Acevedo
*Assistant Examiner* — Manahil Mirghani Ali Abdalhameed
(74) *Attorney, Agent, or Firm* — NORTON ROSE FULBRIGHT US LLP

(57) ABSTRACT

A crystal form of a compound of formula (I), a preparation method therefor, and an application of the crystal form in the preparation of a drug for treating related diseases.

(I)

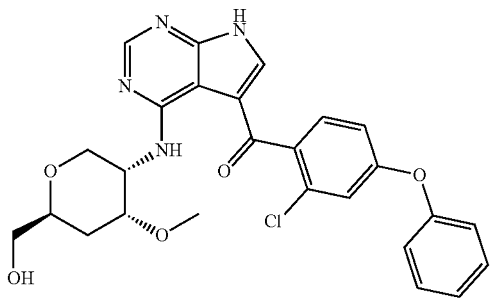

17 Claims, 6 Drawing Sheets

CRYSTAL FORM OF PYRROLOPYRIMIDINE COMPOUND AND PREPARATION METHOD FOR CRYSTAL FORM

CROSS-REFERENCE TO RELATED APPLICATIONS

This application is a national phase application under 35 U.S.C. § 371 of International Application No. PCT/CN2022/092059, filed May 10, 2022, which claims priority to and the benefit of Chinese Application No. 202110518999.9, filed May 12, 2021. The contents of the referenced patent applications are incorporated into the present application by reference.

TECHNICAL FIELD

The present application relates to crystalline forms of compounds of formula (I), and a preparation method thereof, and an application of the crystal form in the preparation of a drug for treating related diseases.

BACKGROUND

Kinases are a class of enzymes that control the transfer of phosphate groups from phosphate donors (such as ATP) to specific substrates. Protein kinase is a large subset of kinases, plays a core role in adjusting various cell signals and processes, and BTK is one of the multiple cell signals.

BTK is a member of the TEC family kinases (TEKs). The family has 5 members, in addition to BTK, there are ITK, TEC, BMX, and TXK. TFKs have an evolutionary history of more than 600 million years and belong to a very ancient family of kinases that function mainly in the hematopoietic system.

BTK is mainly responsible for the conduction and amplification of internal and external signals of various cells in B lymphocytes and is necessary for B cell maturation. Inactivation of BTK function in XLA patients results in a deficiency of peripheral B cells and immunoglobulins. Signal receptors upstream of BTK include growth factors, cytokine receptors, G protein coupled receptors such as chemokine receptors, antigen receptors (especially B cell receptors [BCR]) and integrins. BTK in turn activates many primary downstream signaling pathways, including the phosphoinositide-3 kinase (PI3K)-AKT pathway, phospholipase-C (PLC), protein kinase C and nuclear factor kappa B (NF-κB), etc. The role of BTK in BCR signaling and cell migration is well established, and these functions also appear to be major targets of BTK inhibitor. Increased BTK activity has been detected in blood cancer cells such as B-cell chronic lymphocytic leukemia (CLL) and mantle cell lymphoma (MCL), etc. Abnormal activity of BTK function frequently leads to B-cell malignancies or autoimmune diseases, making it a popular target for research and development.

SUMMARY OF THE INVENTION

The application provides the crystal form A of the compound shown in formula (I), characterized in that the X-ray powder diffraction pattern has a characteristic diffraction peak at the following 2θ angles: 16.16±0.20°, 16.60±0.20°, 22.02±0.20°, 23.08±0.20°.

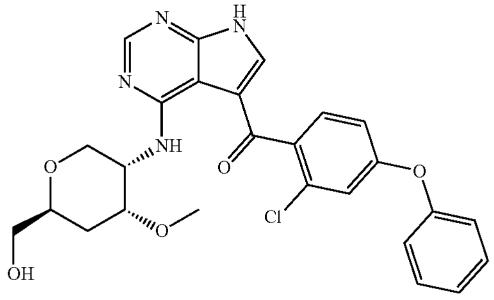

(I)

In some embodiments of this application, the crystal form A of the above compound of formula (I) has an X-ray powder diffraction pattern, indicated by a 2θ angle, comprising at least 5, 6, 7, or 8 diffraction peaks selected from the following: 7.51±0.20°, 10.63±0.20°, 15.06±0.20°, 16.16±0.20°, 16.60±0.20°, 16.60±0.20°, 16.60±0.20°, 21.28±0.20°, 22.02±0.20°, 23.08±0.20°.

In some embodiments of this application, the X-ray powder diffraction pattern of the crystal form A has characteristic diffraction peaks at the following 2θ angles: 7.51±0.20°, 10.63±0.20°, 15.06±0.20°, 16.16±0.20°, 16.60±0.20°, 21.28±0.20°, 22.02±0.20°, 23.08±0.20°.

In some embodiments of this application, the crystal form A of the above compound of formula (I) has an X-ray powder diffraction pattern, indicated by a 2θ angle, comprising at least 9, 10, 11, or 12 diffraction peaks selected from the following: 7.51±0.20°, 10.63±0.20°, 12.00±0.20°, 13.17±0.20°, 15.06±0.20°, 16.16±0.20°, 16.60±0.20°, 18.61±0.20°, 21.28±0.20°, 22.02±0.20°, 22.49±0.20°, 23.08±0.20°.

In some embodiments of this application, the X-ray powder diffraction pattern of the crystal form A has characteristic diffraction peaks at the following 2θ angles: 7.51±0.20°, 10.63±0.20°, 12.00±0.20°, 13.17±0.20°, 15.06±0.20°, 16.16±0.20°, 16.60±0.20°, 18.61±0.20°, 21.28±0.20°, 22.02±0.20°, 22.49±0.20°, 23.08±0.20°.

In some embodiments of this application, the crystal form A of the above compound of formula (I) has an X-ray powder diffraction pattern with diffraction peaks at the following 2θ angles: 7.51°, 9.45°, 10.04°, 10.63°, 12.00°, 13.17°, 14.25°, 15.06°, 15.51°, 16.16°, 16.60°, 17.31°, 17.58°, 18.61°, 18.95°, 19.53°, 20.07°, 20.60°, 21.28°, 21.78°, 22.02°, 22.49°, 23.08°.

In some embodiments of this application, the XRPD profile of the crystal form A is shown in FIG. 1.

In some embodiments of this application, the XRPD spectrum analysis data of the crystal form A is shown in Table 1.

TABLE 1

Analyzed XRPD analysis data for crystal form A

| No. | 2θ angle (°) | Surface Spacing (Å) | Intensity (cts) | Relative Intensity (%) |
|---|---|---|---|---|
| 1 | 7.51 | 11.78 | 1305.31 | 18.69 |
| 2 | 9.45 | 9.36 | 154.36 | 2.21 |
| 3 | 10.04 | 8.81 | 390.64 | 5.59 |
| 4 | 10.63 | 8.32 | 1245.87 | 17.84 |
| 5 | 12.00 | 7.37 | 746.15 | 10.68 |
| 6 | 13.17 | 6.72 | 667.11 | 9.55 |
| 7 | 14.25 | 6.22 | 293.71 | 4.20 |
| 8 | 15.06 | 5.88 | 1489.10 | 21.32 |

TABLE 1-continued

| Analyzed XRPD analysis data for crystal form A | | | | |
|---|---|---|---|---|
| No. | 2θ angle (°) | Surface Spacing (Å) | Intensity (cts) | Relative Intensity (%) |
| 9 | 15.51 | 5.71 | 394.03 | 5.64 |
| 10 | 16.16 | 5.49 | 1551.74 | 22.21 |
| 11 | 16.60 | 5.34 | 6985.46 | 100.00 |
| 12 | 17.31 | 5.12 | 517.26 | 7.40 |
| 13 | 17.58 | 5.05 | 460.56 | 6.59 |
| 14 | 18.61 | 4.77 | 946.34 | 13.55 |
| 15 | 18.95 | 4.68 | 207.76 | 2.97 |
| 16 | 19.53 | 4.55 | 642.54 | 9.20 |
| 17 | 20.07 | 4.42 | 511.08 | 7.32 |
| 18 | 20.60 | 4.31 | 157.42 | 2.25 |
| 19 | 21.28 | 4.18 | 1323.42 | 18.95 |
| 20 | 21.78 | 4.08 | 2127.34 | 30.45 |
| 21 | 22.02 | 4.04 | 2231.97 | 31.95 |
| 22 | 22.49 | 3.95 | 668.70 | 9.57 |
| 23 | 23.08 | 3.85 | 2800.13 | 40.09 |

In some embodiments of this application, the differential scanning calorimetry curve of the crystal form A shows an endothermic peak at 145.7° C.±3.0° C., 208.9° C.±3.0° C., and 218.7° C.±3.0° C.

In some embodiments of this application, the DSC pattern of the crystal form A is shown in FIG. 2.

In some embodiments of this application, the thermogravimetric curve of the crystal form A gives apparent weight change peak at 200.0° C.±3.0° C., with 7.66% of weight loss.

In some embodiments of this application, the TGA pattern of the crystal form A is shown in FIG. 3.

The application provides the crystal form B of the compound shown in formula (I), characterized in that the X-ray powder diffraction pattern has a characteristic diffraction peak at the following 2θ angles: 7.47±0.20°, 10.41±0.20°, 16.04±0.20°, 16.73±0.20°.

(I)

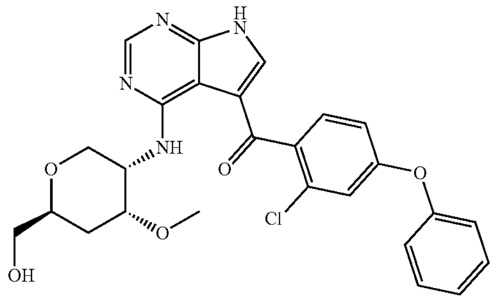

In some embodiments of this application, the crystal form B of the above compound of formula (I) has an X-ray powder diffraction pattern, indicated by a 2θ angle, comprising at least 5, 6, 7, or 8 diffraction peaks selected from the following: 7.47±0.20°, 10.41±0.20°, 15.23±0.20, 16.04±0.20°, 16.73±0.20°, 20.87±0.20°, 21.46±0.20°, 21.91±0.20°.

In some embodiments of this application, the X-ray powder diffraction pattern of the crystal form B has characteristic diffraction peaks at the following 2θ angles: 7.47±0.20°, 10.41±0.20°, 15.23±0.20°, 16.04±0.20°, 16.73±0.20°, 20.87±0.20°, 21.46±0.20°, 21.91±0.20°.

In some embodiments of this application, the crystal form B of the above compound of formula (I) has an X-ray powder diffraction pattern, indicated by a 2θ angle, comprising at least 9, 10, 11, or 12 diffraction peaks selected from the following: 7.47±0.20°, 9.53±0.20°, 10.41±0.20°, 11.91±0.20°, 13.91±0.20°, 15.23±0.20°, 16.04±0.20°, 16.73±0.20°, 18.82±0.20°, 20.87±0.20°, 21.46±0.20°, 21.91±0.20°.

In some embodiments of this application, the X-ray powder diffraction pattern of the crystal form B has characteristic diffraction peaks at the following 2θ angles: 7.47±0.20°, 9.53±0.20°, 10.41±0.20°, 11.91±0.20°, 13.91±0.20°, 15.23±0.20°, 16.04±0.20°, 16.73±0.20°, 18.82±0.20°, 20.87±0.20°, 21.46±0.20°, 21.91±0.20°.

In some embodiments of this application, the crystal form B of the above compound of formula (I) has an X-ray powder diffraction pattern with diffraction peaks at the following 2θ angles: 7.47°, 9.53°, 9.78°, 10.41°, 11.45°, 11.91°, 12.40°, 13.22°, 13.91°, 14.87°, 15.23°, 15.44°, 16.04°, 16.73°, 17.33°, 17.88°, 18.82°, 19.61°, 19.88°, 20.25°, 20.87°, 21.46°, 21.91°.

In some embodiments of this application, the XRPD profile of the crystal form B is shown in FIG. 4.

In some embodiments of this application, the XRPD spectrum analysis data of the crystal form B is shown in Table 2.

TABLE 2

| Analyzed XRPD analysis data for crystal form B | | | | |
|---|---|---|---|---|
| No. | 2θ angle (°) | Surface Spacing (Å) | Intensity (cts) | Relative Intensity (%) |
| 1 | 7.47 | 11.83 | 2210.63 | 22.59 |
| 2 | 9.53 | 9.28 | 775.51 | 7.92 |
| 3 | 9.78 | 9.04 | 389.45 | 3.98 |
| 4 | 10.41 | 8.50 | 2379.92 | 24.32 |
| 5 | 11.45 | 7.73 | 262.47 | 2.68 |
| 6 | 11.91 | 7.43 | 1197.77 | 12.24 |
| 7 | 12.40 | 7.14 | 127.92 | 1.31 |
| 8 | 13.22 | 6.70 | 295.97 | 3.02 |
| 9 | 13.91 | 6.37 | 551.46 | 5.63 |
| 10 | 14.87 | 5.96 | 872.41 | 8.91 |
| 11 | 15.23 | 5.82 | 1424.48 | 14.55 |
| 12 | 15.44 | 5.74 | 289.68 | 2.96 |
| 13 | 16.04 | 5.53 | 1996.67 | 20.40 |
| 14 | 16.73 | 5.30 | 9786.95 | 100.00 |
| 15 | 17.33 | 5.12 | 205.95 | 2.10 |
| 16 | 17.88 | 4.96 | 251.41 | 2.57 |
| 17 | 18.82 | 4.72 | 652.86 | 6.67 |
| 18 | 19.61 | 4.53 | 353.39 | 3.61 |
| 19 | 19.88 | 4.47 | 473.07 | 4.83 |
| 20 | 20.25 | 4.38 | 452.36 | 4.62 |
| 21 | 20.87 | 4.26 | 1496.76 | 15.29 |
| 22 | 21.46 | 4.14 | 1305.89 | 13.34 |
| 23 | 21.91 | 4.06 | 1538.40 | 15.72 |

In some embodiments of this application, the differential scanning calorimetry curve of the crystal form B shows an endothermic peak at 214.3° C.±3.0° C.

In some embodiments of this application, the DSC pattern of the crystal form B is shown in FIG. 5.

In some embodiments of this application, the thermogravimetric curve of the crystal form B gives apparent weight change peak at 200.0° C.±3.0° C., with 0.64% of weight loss.

In some embodiments of this application, the TGA pattern of the crystal form B is shown in FIG. 6.

The application provides the crystal form C of the compound shown in formula (I), characterized in that the X-ray powder diffraction pattern has a characteristic diffraction peak at the following 2θ angles: 5.28±0.20°, 58±0.20°, 20.56±0.20°, 24.55±0.20°

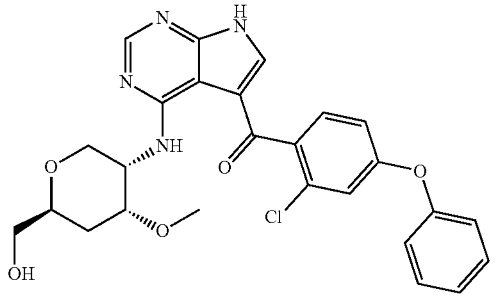

(I)

In some embodiments of this application, the crystal form C of the above compound of formula (I) has an X-ray powder diffraction pattern, indicated by a 2θ angle, comprising at least 5, 6, 7, or 8 diffraction peaks selected from the following: 5.28±0.20°, 8.58±0.20°, 11.00±0.20°, 11.52±0.20°, 15.72±0.20°, 20.56±0.20°, 21.84±0.20°, 24.55±0.20°.

In some embodiments of this application, the X-ray powder diffraction pattern of the crystal form C has characteristic diffraction peaks at the following 2θ angles: 5.28±0.20°, 8.58±0.20°, 11.00±0.20°, 11.52±0.20°, 15.72±0.20°, 20.56±0.20°, 21.84±0.20°, 24.55±0.20°.

In some embodiments of this application, the crystal form C of the above compound of formula (I) has an X-ray powder diffraction pattern, indicated by a 2θ angle, comprising at least 9, 10, 11, or 12 diffraction peaks selected from the following: 5.28±0.20°, 8.58±0.20°, 11.00±0.20°, 11.52±0.20°, 15.72±0.20°, 16.69±0.20°, 17.16±0.20°, 18.62±0.20°, 19.76±0.20°, 20.56±0.20°, 21.84±0.20°, 24.55±0.20°.

In some embodiments of this application, the X-ray powder diffraction pattern of the crystal form C has characteristic diffraction peaks at the following 2θ angles: 5.28±0.20°, 8.58±0.20°, 11.00±0.20°, 11.52±0.20°, 15.72±0.20°, 16.69±0.20°, 17.16±0.20°, 18.62±0.20°, 19.76±0.20°, 20.56±0.20°, 21.84±0.20°, 24.55±0.20°.

In some embodiments of this application, the crystal form C of the above compound of formula (I) has an X-ray powder diffraction pattern with diffraction peaks at the following 2θ angles: 5.28°, 8.58°, 11.00°, 11.52°, 14.08°, 15.08°, 15.72°, 16.69°, 17.16°, 18.62°, 19.76°, 20.56°, 20.77°, 21.84°, 23.14°, 23.89°, 24.55°, 25.40°, 28.24°, 29.21°, 31.36°.

In some embodiments of this application, the XRPD profile of the crystal form C is shown in FIG. 7.

In some embodiments of this application, the XRPD spectrum analysis data of the crystal form C is shown in Table 3.

TABLE 3

Analyzed XRPD analysis data for crystal form C

| No. | 2θ angle (°) | Surface Spacing (Å) | Intensity (cts) | Relative Intensity (%) |
|---|---|---|---|---|
| 1 | 5.28 | 16.73 | 2228.08 | 100.00 |
| 2 | 8.58 | 10.31 | 1259.71 | 56.54 |
| 3 | 11.00 | 8.05 | 718.79 | 32.26 |
| 4 | 11.52 | 7.68 | 533.40 | 23.94 |
| 5 | 14.08 | 6.29 | 166.48 | 7.47 |
| 6 | 15.08 | 5.88 | 183.33 | 8.23 |
| 7 | 15.72 | 5.64 | 468.50 | 21.03 |

TABLE 3-continued

Analyzed XRPD analysis data for crystal form C

| No. | 2θ angle (°) | Surface Spacing (Å) | Intensity (cts) | Relative Intensity (%) |
|---|---|---|---|---|
| 8 | 16.69 | 5.31 | 276.86 | 12.43 |
| 9 | 17.16 | 5.17 | 397.64 | 17.85 |
| 10 | 18.62 | 4.77 | 347.48 | 15.60 |
| 11 | 19.76 | 4.49 | 375.29 | 16.84 |
| 12 | 20.56 | 4.32 | 1098.51 | 49.30 |
| 13 | 20.77 | 4.28 | 683.95 | 30.70 |
| 14 | 21.84 | 4.07 | 587.28 | 26.36 |
| 15 | 23.14 | 3.84 | 181.31 | 8.14 |
| 16 | 23.89 | 3.72 | 265.72 | 11.93 |
| 17 | 24.55 | 3.63 | 730.49 | 32.79 |
| 18 | 25.40 | 3.51 | 246.43 | 11.06 |
| 19 | 28.24 | 3.16 | 106.89 | 4.80 |
| 20 | 29.21 | 3.06 | 185.64 | 8.33 |
| 21 | 31.36 | 2.85 | 63.86 | 2.87 |

In some embodiments of this application, the differential scanning calorimetry curve of the crystal form C shows an endothermic peak at 218.8° C.±3.0° C.

In some embodiments of this application, the DSC pattern of the crystal form C is shown in FIG. 8.

In some embodiments of this application, the thermogravimetric curve of the crystal form C is 200.0° C.±3.0° C., the weight loss reaches 1.45%.

In some embodiments of this application, the TGAprofile of the crystal form C is shown in FIG. 9.

The present application also provides applications of the above crystalline type A or crystalline type B or crystalline type C in the preparation of drugs for the treatment of diseases associated with BTK protein kinase.

In some embodiments of this application, the above BTK protein kinase-related disorders are hematologic tumors.

Technical Effect

The compounds of the present application have good crystalline stability and are easy to be drugged. They have significant tumor growth inhibiting effects.

Definition and Description

Unless otherwise specified, the following terms and phrases used herein are intended to have the following meanings. A specific term or phrase should not be considered indefinite or unclear in the absence of a particular definition, and it should be understood in the conventional sense. When a trade name appears herein, it is intended to refer to its corresponding commodity or active ingredient thereof.

Reference throughout this specification to "an embodiment" or "an embodiment" or "in another embodiment" or "in another embodiment" means including, in at least one embodiment, a particular reference element, structure, or feature related to the embodiment. Accordingly, the phrases "in an embodiment" or "in an embodiment" or "in another embodiment" or "in certain embodiments" appearing at various locations throughout the specification need not all refer to the same embodiment. Furthermore, specific elements, structures, or features may be combined in any suitable manner in one or more embodiments.

It should be noted that the singular forms (such as "a", "an" and "the") used in the specification and additional claims of this application include plural objects unless expressly specified herein. Thus, for example, a reaction including a "catalyst" includes a catalyst, or two or more catalysts. It should also be understood that the term "or" is generally used in its meaning including "and/or" unless expressly specified herein.

The intermediate compound of the present application can be prepared by a variety of synthetic methods well known to those skilled in the art, including the specific embodiments listed below, the embodiments formed by its combination with other chemical synthesis methods, and the methods described by those skilled in the art Known equivalent alternatives, preferred implementations include but are not limited to the examples of this application.

The chemical reactions in the specific embodiments of the present application are completed in a suitable solvent, and the solvent must be suitable for the chemical changes of the present application and the reagents and materials required therefor. In order to obtain the compounds of the present application, it is sometimes necessary for those skilled in the art to modify or select synthetic steps or reaction schemes on the basis of existing embodiments.

The structure of the compounds of the present invention can be confirmed by conventional methods known to those skilled in the art. If the present invention involves the absolute configuration of the compound, the absolute configuration can be confirmed by conventional technical means in the art. For example, single crystal X-ray diffraction (SXRD), the cultured single crystal is collected with a Bruker D8 venture diffractometer to collect diffraction intensity data, the light source is CuKα radiation, and the scanning method is φ/ω scanning. After collecting relevant data, the direct method is further adopted (Shelxs97) By analyzing the crystal structure, the absolute configuration can be confirmed.

The present application will be specifically described through examples below, and these examples do not imply any limitation to the present application.

All solvents used in this application were commercially available and used without further purification.

Compounds were named by manually or ChemDraw® software, and the commercially available compounds adopt the supplier catalog name.

The powder X-ray diffraction (XRPD) method of this application.

Instrument Model: PANalytical X'pert3 X-Ray Diffractometer.

Test method: About 10-20 mg of sample is used for XRPD detection.

The detailed XRPD parameters are as follows:

Light pipe: Cu, kα1, λ=1.54060 Å, kα2, λ=1.54443 Å

Phototube voltage: 45 kV, phototube current: 40 mA

Divergence slit: 0.60 mm

Detector slit: 10.50 mm

Anti-scatter slit: 7.10 mm

Scanning range: 3-40 deg

Step diameter: 0.0263 deg

Scanning time (Scan Step Time): 46.665s

Sample disk speed: 15 rpm

The differential thermal analysis (DSC) method of this application.

Instrument Model: TA 2500 Differential Scanning calorimeter

Test method: Take a sample (about 1 mg) and place it in a DSC aluminum pan for testing. Under N2 conditions, heat the sample from 25° C. to 350° C. at a heating rate of 10° C./min.

The thermal gravimetric analysis (TGA) method of this application.

Instrument Model: TA 5500 Thermogravimetric Analyzer

Test method: Take a sample (2-5 mg) and place it in a TGA aluminum pan and open the cover for testing. Under N2 conditions, heat the sample from room temperature to 350° C. at a heating rate of 10° C./min.

The vapor adsorption analysis (DVS) method of this application.

Instrument model: SMS DVS Advantage dynamic vapor adsorption instrument

Test conditions: Take a sample (10-15 mg) and place it in a DVS sample tray for testing.

The detailed DVS parameters are as follows:

Temperature: 25° C.

Balance: dm/dt=0.01%/min (shortest: 10 min, longest: 180 min)

Drying: 120 min at 0% RH

RH (%) test rang: 10%

RH (%) test range: 0%-90%-0%

The classification of hygroscopicity evaluation is shown in Table 4:

TABLE 4

Humidity evaluation classification

| Hygroscopicity Classification | ΔW % |
|---|---|
| deliquescence | Absorb enough water to form a liquid |
| Very hygroscopic | ΔW % ≥ 15% |
| Hygroscopic | 15% > ΔW % ≥ 2% |
| slightly hygroscopic | 2% > ΔW % ≥ 0.2% |
| No or almost no hygroscopicity | ΔW % < 0.2% |

Note:
ΔW % represents the moisture absorption weight gain of the test product at 25 ± 1° C. and 80 ± 2% RH.

DETAILED DESCRIPTION OF THE EMBODIMENTS

Figure 1:
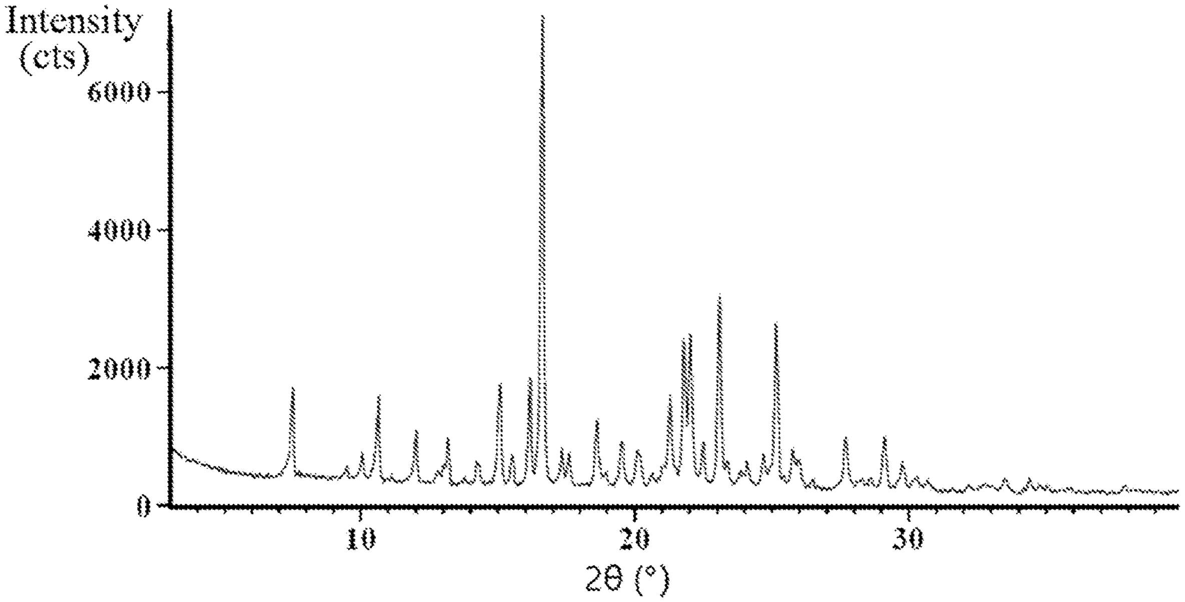
FIG. 1 is the XRPD spectrogram of the Cu-Kα radiation of formula (I) compound crystal form A.

In order to better understand the content of the present application, the following will be further described in conjunction with specific examples, but the specific implementation manners are not intended to limit the content of the present application.

Reference Example

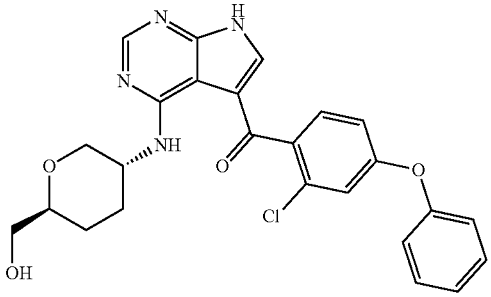 [SMILES: O=C(c1ccc(Oc2ccccc2)cc1Cl)c1c[nH]c2ncnc(N[C@@H]3CC[C@@H](CO)OC3)c12]

Reference example is prepared by the method described in patent WO2017111787 Compound (I).

Embodiment 1: The Preparation of Formula (I) Compound (I)

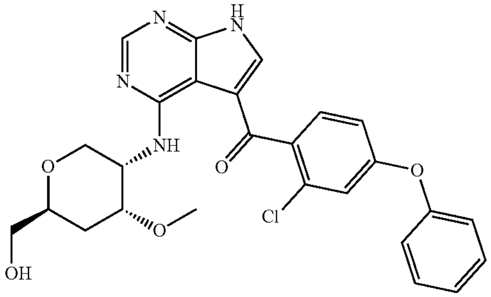

Synthetic Route:

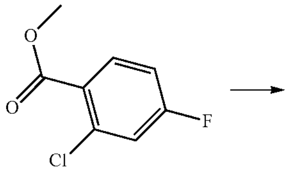

A1

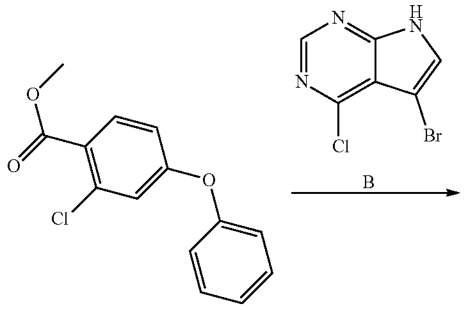

A2

-continued

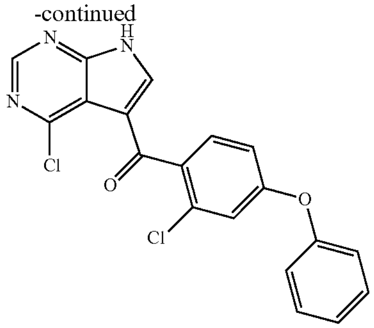

A

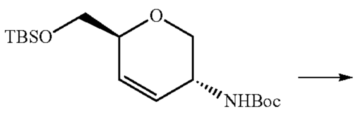

1-1

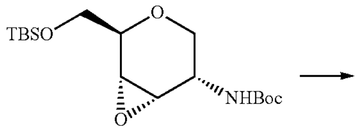

1-2

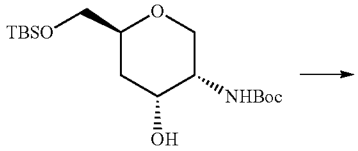

1-3

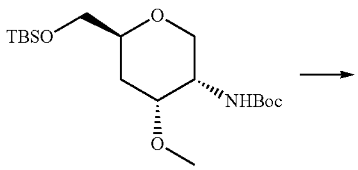

1-4

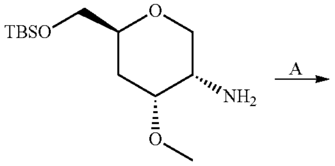

1-5

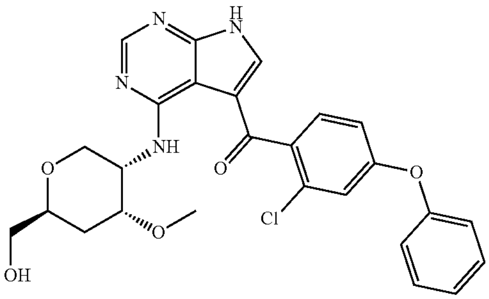

I

Step 1: Synthesis of Compound A2

Phenol (7.49 g, 79.54 mmol, 7.00 mL, 1.5 eq), compound A1 (10 g, 53.03 mmol, 1 eq), cesium carbonate (25.92 g, 79.54 mmol, 1.5 eq) were dissolved in N, N-dimethylformamide (20 mL), reacted at 80° C. for 3 hours. After the reaction, the reaction solution was filtered, water was added, extracted with ethyl acetate (100 mL×3). Organic phases were combined, dried over anhydrous sodium sulfate, and rotavaporated to dryness. The crude was purified by column chromatography (petroleum ether:ethyl acetate=10:1), to obtain compound A2. LCMS: (ESI) m/z:263.1 $[M+1]^+$.

Step 2: Synthesis of Compound A

Compound B (6 g, 25.81 mmol, 1 eq) was added to tetrahydrofuran (180 mL). The mixture was cooled to −78° C. (suspension, partially dissolved), and then n-butyllithium (2.5 M, 21.68 mL, 2.1 eq) was added dropwise. After dropping, the solution was stirred and reacted at −78° C. for 1 hour. Compound A2 (7.12 g, 27.10 mmol, 1.05 eq) in tetrahydrofuran (10 mL) was added dropwise, and stirring continued for 1 hour. After the reaction was completed, the reaction was quenched with saturated ammonium chloride and stirred for 5 minutes. Organic phase was separated, and the aqueous phase was extracted with ethyl acetate (100 mL×3). The organic phases were combined and concentrated to obtain crude intermediate A. LCMS: (ESI) m/z: 384.2 $[M+1]^+$.

Step 3: Synthesis of Compound 1-2

To a solution of Compound 1-1 (10 g, 29.11 mmol, 1 eq) dissolved in dichloromethane (100 mL), m-chloroperoxybenzoic acid (7.53 g, 43.66 mmol, 1.5 eq) was added at 0° C. Reaction ran at 20° C. for 15 hours. Saturated sodium sulfite solution was added to quench the reaction. The mixture was extracted with ethyl acetate (50 mL×3), washed with saturated brine, dried over anhydrous sodium sulfate, and concentrated to obtain a crude product, which was purified by column chromatography (petroleum ether:ethyl acetate=10:1) to obtain compound 1-2. LCMS: (ESI) m/z: 304.2 [M-t-Bu+1].

Step 4: Synthesis of Compounds 1-3

Compound 1-2 (5 g, 13.91 mmol, 1 eq) was dissolved in tetrahydrofuran (10 mL), lithium aluminum tetrahydride (2.5 M, 8.34 mL, 1.5 eq) was added at −20° C. and reacted at 20° C. for 3 hours after the addition was complete. After the reaction was completed, sodium hydroxide solution was added to quench the reaction. The forming solid was filtered off, and washed with ethyl acetate to give the filtrate, which was concentrated to obtain a crude product. The crude product was purified by column chromatography (petroleum ether:ethyl acetate=3:1) to obtain compound 1-3. LCMS: (ESI) m/z: 306.1 [M-t-Bu+1].

Step 5: Synthesis of Compounds 1-4

Compound 1-3 (0.117 g, 323.61 μmol, 1 eq) was dissolved in acetonitrile (2 mL). Under nitrogen protection, silver oxide (224.97 mg, 970.83 μmol, 3 eq) and iodomethane (459.33 mg, 3.24 mmol, 201.46 μL, 10 eq) were sequentially added at 20° C. The mixture was heated at 80° C. for 12 hours. After cooling, the forming solid was filtered, and the filtrate was rotavaporated to obtain compound 1-4, which was used directly to the next step without further purification. LCMS: (ESI) m/z: 319.85 [M-t-Bu+1].

Step 6: Synthesis of Compounds 1-5

Compound 1-4 (121.54 mg, 323.61 μmol, 1 eq) in dichloromethane (2 mL), was added by trifluoroacetic acid (30.80 mg, 270.12 μmol, 0.02 mL, 0.84 eq), The reaction ran at 20° C. for 1 hour. The reaction solution was directly rotavaporated to obtain compound 1-5. Compounds 1-5 were directly used in the next reaction without purification. LCMS: (ESI) m/z: 276.20 $[M+H]^+$.

Step 7: Synthesis of the Compound of Formula (I)

Compound A (99.47 mg, 258.89 μmol, 0.8 eq) and compound 1-5 (89.14 mg, 323.61 μmol, 1 eq) were dissolved in isopropanol (2 mL), and N,N-diisopropylethylamine (104.56 mg, 809.03 μmol, 140.91 μL, 2.5 eq). It was then microwaved at 130° C. for 1 hour. The crude product was obtained after the reaction solution was rotavaporated. The crude product was purified (chromatographic column: Phenomenex Gemini-NX 80 mm*40 mm*3 μm; mobile phase: [water (0.05% $NH_3H_2O$+10 mM $NH_4HCO_3$)-acetonitrile]; B (acetonitrile) %: 37%-57%, 8 min) to obtain the compound of formula (I). LCMS: (ESI) m/z: 508.9 $[M+H]^+$ $^1H$ NMR (400 MHz, $CDCl_3$) δ 9.25 (d, J=8.3 Hz, 1H), 8.35 (s, 1H), 7.50-7.39 (m, 3H), 7.39-7.32 (m, 1H), 7.28-7.22 (m, 1H), 7.14-7.08 (m, 3H), 6.98 (dd, J=2.3, 8.3 Hz, 1H), 4.57 (br. d, J=5.5 Hz, 1H), 4.08 (dd, J=5.4, 10.2 Hz, 1H), 3.93-3.82 (m, 2H), 3.81-3.69 (m, 2H), 3.64-3.53 (m, 4H), 2.03 (br. d, J=13.1 Hz, 1H), 1.70 (br. s, 1H).

Embodiment 2: Preparation of the Crystal Form a of the Compound of Formula (I)

Compound A (3.01 g, 7.81 mmol, 1.0 eq) and compound 1-5 (1.62 g, 8.20 mmol, 1.05 eq) were dissolved in isopropanol (15 mL), and N,N-diisopropylethylamine (3.03 g, 23.4 mmol, 3.0 eq). The mixture was reacted at 90° C. for 20 hours. After LCMS detection of reaction completeness, 50 mL of water was added. The mixture was extracted with 100 mL of ethyl acetate, which was collected, dried over anhydrous sodium sulfate, and evaporated under reduced pressure. The crude was triturated by ethyl acetate at room temperature to obtain a solid product, which is the crystal form A of the compound of formula (I).

Embodiment 3: Preparation of the Crystal Form B of the Compound of Formula (I)

About 100 mg of the compound of crystal type A was added to different 2.0 mL glass vials, respectively, and 1 mL of solvent or solvent mixture was added to obtain the suspension, the suspension samples were placed in a magnetic heating stirrer and stirred at 25° C. for 16 h. The suspension was centrifuged, and vacuum-dried at 40° C. for 60 hours to constant weight to obtain the crystal form B of the compound of formula (I) (as shown in Table 5).

TABLE 5

Different solvent crystal form screening experiments

| No. | Solvent | Temperature (° C.) | State | Crystal Form |
|---|---|---|---|---|
| 1 | Methanol | 25 | white suspension | Form B |
| 2 | ethanol | 25 | white suspension | Form B |
| 3 | Acetonitrile | 25 | white suspension | Form B |
| 4 | Methanol:water = 1:1 | 25 | white suspension | Form B |
| 5 | Ethanol:water = 2:1 | 25 | white suspension | Form B |

Embodiment 4: Preparation of the Crystal Form C of the Compound of Formula (I)

The compound of 1.2 g of crystal form A is dispersed in 12 mL of methyl tert-butyl ether to form a suspension, the system is stirred at 25° C., 40° C. or 60° C. for 16 hours, filtered, and the filter cake is vacuum dried at 40° C. for 60 hours to a constant weight to obtain the crystal form C of the compound of formula (I).

TABLE 6

Form C obtained under different temperature

| No. | Solvent | Temperature (° C.) | State | Crystal Form |
|---|---|---|---|---|
| 1 | methyl tert-butyl ether | 25 | white suspension | Form C |
| 2 | methyl tert-butyl ethe | 40 | white suspension | Form C |
| 3 | methyl tert-butyl ethe | 60 | white suspension | Form C |

Embodiment 5: Competitive Experiment of Crystal Form B and Crystal Form C

Three groups of 30 mg crystal form B and 30 mg crystal form C compounds were respectively added to different 2.0 mL glass vials, and 0.6 mL methyl tert-butyl ether was added to obtain a suspension, and the suspension samples were placed in the magnetic heating stirrer was stirred at 20° C., 40° C. and 60° C. for 16 hours, the suspension was centrifuged to obtain a white solid, and the crystal form C of the compound of formula (I) was obtained by vacuum drying to constant weight.

TABLE 7

Competitive experiments of Form B and Form C

| No. | Solvent | Temperature (° C.) | Solvent Volume (mL) | State | Crystal Form |
|---|---|---|---|---|---|
| 1 | methyl tert-butyl ether | 20 | 0.6 | white suspension | Form C |
| 2 | methyl tert-butyl ether | 40 | 0.6 | white suspension | Form C |
| 3 | methyl tert-butyl ether | 60 | 0.6 | white suspension | Form C |

Conclusion: Compared with Form B, Form C is more stable.

Embodiment 6 Hygroscopicity Research of Formula (I) Compound Crystal Form C

Experimental Materials

SMS DVS Advantage dynamic vapor adsorption instrument

Experimental Method

Taking 10-15 mg of compound crystal form C of formula (I) and placing it in a DVS sample tray for testing.

Experimental Results

Figure 10:
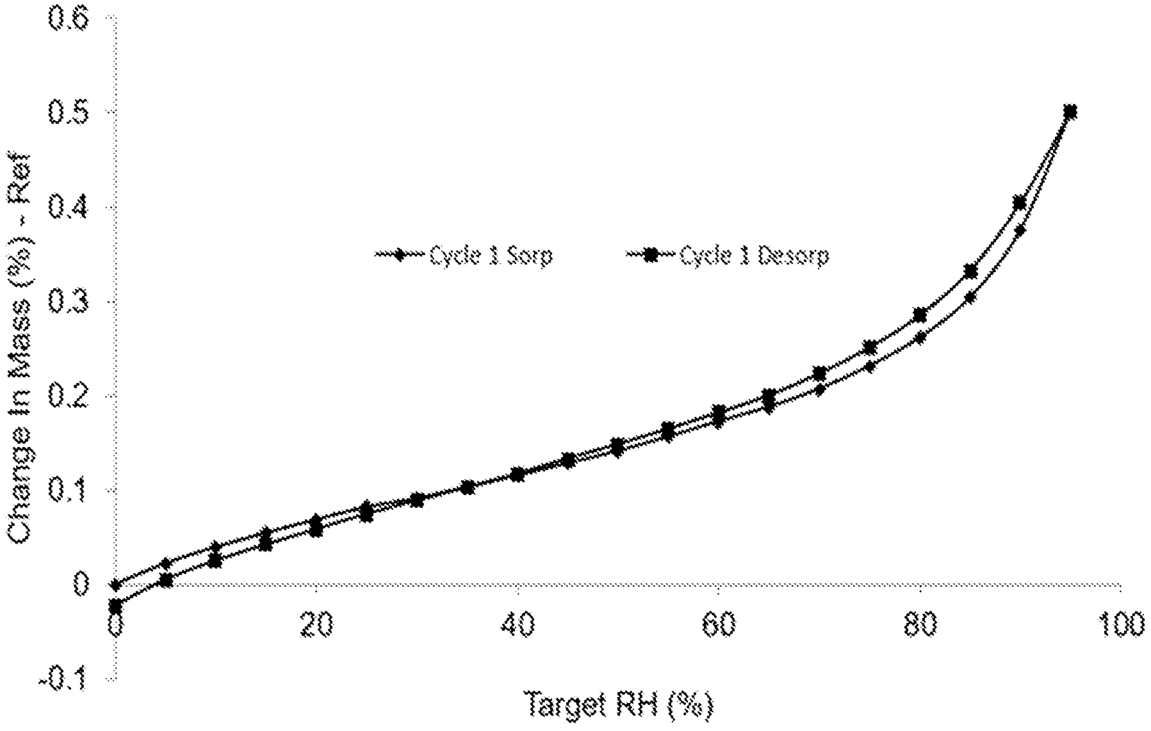
FIG. 10 is the DVS spectrogram of formula (I) compound crystal form C.

The DVS spectrum of the crystal form C of the compound of formula (I) is shown in FIG. 10, ΔW=0.262%.

Experimental Conclusion

The hygroscopic weight gain of the crystal form C of the compound of formula (I) at 25° C. and 80% RH is 0.262%, which is slightly hygroscopic.

Embodiment 7: The Solid Stability Test of Formula (I) Compound Crystal Form C

According to the "Guiding Principles for Stability Testing of Raw Materials and Preparations" (Chinese Pharmacopoeia 2015 Edition Four General Rules 9001), the crystal form C of the compound of formula (I) was investigated for its stability under high temperature (60° C., open), high humidity (a. room temperature/relative humidity 92.5%, open; b. 40° C./75% relative humidity, open; c. 60° C./75% relative humidity, open) and the stability under strong light (5000 1×, airtight).

The crystal form C (15 mg) of the compound of formula (I) is weighed and placed on the bottom of the glass sample bottle to be spread into a thin layer. Samples placed under high-temperature and high-humidity conditions are sealed with aluminum foil, and small holes are formed on the aluminum foil to ensure that the samples can fully contact with the ambient air; and the sample placed under the strong illumination condition is sealed by a threaded bottle cap. Samples placed under different conditions were sampled and tested (XRPD) on the 5th day, 10th day, and 1 month. The test results were compared with the initial test results on day 0. The test results are shown in Table 8 below:

TABLE 8

Solid stability test result of the crystal form C of the compound of formula (I)

| Experimental Condition | Time Point | Crystal Form |
|---|---|---|
| — | 0 day | Form C |
| High temperature (60° C., open) | 5th day | Form C |
| | 10th day | Form C |
| High humidity (room temperature/relative humidity 92.5%, open) | 5th day | Form C |
| | 10th day | Form C |
| High humidity (40° C./75% relative humidity, open) | 1 month | Form C |
| High humidity (60° C./75% relative humidity, open) | 1 month | Form C |
| Strong light (5000 1x, airtight) | 10th day | Form C |

Conclusion: The crystal form C of the compound of formula (I) has good stability under high temperature, high humidity and strong light conditions.

Biological Test Data:

Experimental Example 1: BTK Enzyme Activity Test

The specific experimental process of BTK enzyme activity test is as follows:

Buffer: 20 mM hydroxyethylpiperazine ethylsulfuric acid (Hepes) (pH 7.5), 10 mM magnesium chloride, 1 mM ethylene glycol bisaminoethyl ether tetraacetic acid (EGTA), 0.02% polyoxyethylene lauryl ether (Brij35), 0.02 mg/mL BSA, 0.1 mM sodium vanadate ($Na_3VO_4$), 2 mM dithiothreitol (DTT), 1% DMSO, 200 μM adenosine triphosphate (ATP).

1. Configuring the substrate in the newly prepared reaction buffer
2. Adding the required cofactors to the above substrate solution 3. Adding the kinase $BTK^{C481S}$ to the above substrate solution and mixing well
4. Adding the compound dissolved in DMSO to the kinase reaction mixture through Echo550 (Acoustic technology; nanoliter range), and incubating at room temperature for 20 minutes
5. Adding $^{33}$P-ATP (with a specific activity of 10 μCi/μL) into the reaction mixture to initiate the reaction
6. Incubating at room temperature for 2 hours
7. Detection of radioactivity by filtration-binding method
8. Kinase activity data represent the percentage of remaining kinase activity in the test sample compared to the vehicle (dimethyl sulfoxide) reaction. Using Prism (GraphPad software) to obtain $IC_{50}$ values and fitting curves, and the results are shown in Table 9.

TABLE 9

| BTK in vitro activity test results | |
|---|---|
| No. | $BTK^{C481S}$ $IC_{50}$ (nM) |
| Compound of formula (I) | 7.3 |

Conclusion: the compound of formula (I) has strong inhibitory effect on BTK C481S mutation.

Experimental Example 2: Pharmacokinetic Evaluation of Formula (I) Compound in Mice 2.1 Purpose of the Experiment: Pharmacokinetics (Intravenous) of Test Compounds in CD-1 Mice The compound of formula (I) and the reference example were mixed with vehicle 0.10 mg/mL in 10% NMP/60% PEG400/30% $H_2O$, vortexed and sonicated to prepare a 0.1 mg/mL clear solution. Select CD-1 male mice aged 7 to 10 weeks and administer the candidate compound solution intravenously at a dose of 0.21 mg/kg.

The whole blood was collected for a certain period of time to prepare plasma, and the drug concentration was analyzed by LC-MS/MS method. Pharmacokinetic parameters were calculated by Phoenix WinNonlin software (Pharsight, USA). The results were shown in Table 10.

TABLE 10

| Intravenous (IV) PK data | | |
|---|---|---|
| Testing Sample | Reference Example | Compound of Formula (I) |
| Dosage (mg/kg) | 0.21 | 0.21 |
| Unbound PPB | 0.2% | 0.4% |
| $C_0$ (nM) | 1038 | 562 |
| $T_{1/2}$ (h) | 4.34 | 4.65 |
| Vd (L/kg) | 0.70 | 0.85 |
| Cl (mL/Kg/min) | 2.01 | 2.12 |
| $AUC_{0-inf}$ (nM · h) | 3493 | 3107 |
| $AUC_u$ (nM · h) | 7.0 | 12.4 |

Note:
$AUC_u = AUC_{0-inf} \times$ Unbound PPB (Mouse)

Conclusion: The free drug concentration of the compound of formula (I) in mouse plasma is higher than that of the reference compound.

2.2 Purpose of the Experiment: Pharmacokinetics of the Test Compound in CD-1 Mice (Oral Administration)

The compound of formula (I) and the reference example were mixed with vehicle 10% NMP/60% PEG400/30% $H_2O$, vortexed and sonicated to prepare a 0.6 mg/mL clear solution. Male CD-1 mice aged 7 to 10 weeks were selected, and the candidate compound solution was administered orally by gavage at a dose of 3.1 mg/kg. Whole blood was collected for a certain period of time to prepare plasma, and the drug concentration was analyzed by LC-MS/MS. Pharmacokinetic parameters were calculated with Phoenix WinNonlin software (Pharsight, USA). The results were shown in Table 11.

TABLE 11

| Oral (PO) PK Data | | |
|---|---|---|
| Testing Sample | Reference Example | Compound of Formula (I) |
| Dosage (mg/kg) | 3.1 | 3.1 |
| Unbound PPB | 0.2% | 0.4% |
| $C_{max}$ (nM) | 3835 | 2975 |
| Tmax | 8.0 | 6 |
| $T_{1/2}$ (h) | 3.75 | 3.73 |
| $AUC_{0-inf}$ (nM · h) | 44124 | 33246 |
| $AUC_u$ (nM · h) | 88.2 | 133.0 |

Note:
$AUC_u = AUC_{0-inf} \times$ Unbound PPB (Mouse)

Conclusion: The free drug concentration of the compound of formula (I) in mouse plasma is higher than that of the reference compound.

Experimental Example 3: Pharmacokinetic Evaluation of Compounds in Rats 3.1 Purpose of the Experiment: Pharmacokinetics (Intravenous) of the Test Compound in SD Rats.

The compound of formula (I) and the reference example were mixed with vehicle 0.10 mg/mL in 10% NMP/60% PEG400/30% $H_2O$, vortexed and sonicated to prepare a 0.5 mg/mL clear solution. SD rats aged 7 to 10 weeks were selected and given the candidate compound solution intravenously. Whole blood was collected for a certain period of time to prepare plasma, and the drug concentration was analyzed by LC-MS/MS. Pharmacokinetic parameters were calculated with Phoenix WinNonlin software (Pharsight, USA). The results were shown in Table 12.

TABLE 12

| Intravenous (IV) PK data | | |
|---|---|---|
| Testing Sample | Reference Example | Compound of Formula (I) |
| Dosage (mg/kg) | 0.51 | 0.49 |
| Unbound PPB | 0.1% | 0.2% |
| $C_0$ (nM) | 800 | 852 |
| $T_{1/2}$ (h) | 2.02 | 1.82 |
| Vd (L/kg) | 1.57 | 1.42 |
| Cl (mL/Kg/min) | 9.08 | 9.80 |
| $AUC_{0-inf}$ (nM · h) | 1922 | 1695 |
| $AUC_u$ (nM · h) | 1.9 | 3.4 |

Note:
$AUC_u = AUC_{0-inf} \times$ Unbound PPB (Rat in vivo test PPB)

Conclusion: The free drug concentration of the compound of formula (I) in rat plasma is higher than that of the reference compound.

3.2 Purpose of the Experiment: Pharmacokinetics of the Test Compound in SD Rats (Oral)

The compound of formula (I) and the reference example were mixed with vehicle 10% NMP/60% PEG400/30% $H_2O$, vortexed and sonicated to prepare a 2 mg/mL clear solution. SD rats aged 7 to 10 weeks were selected, and the candidate compound solution was administered orally.

Whole blood was collected for a certain period of time to prepare plasma, and the drug concentration was analyzed by LC-MS/MS method, and the pharmacokinetic parameters were calculated by Phoenix WinNonlin software (Pharsight, USA). The results are shown in Table 13.

TABLE 13

Oral (PO) PK Data

| Testing Sample | Reference Example | Compound of Formula (I) |
|---|---|---|
| Dosage (mg/kg) | 1.9 | 1.8 |
| Unbound PPB | 0.1% | 0.2% |
| $C_{max}$ (nM) | 607 | 587 |
| Tmax | 2.00 | 2.00 |
| $T_{1/2}$ (h) | 2.41 | 2.33 |
| $AUC_{0\text{-}inf}$ (nM · h) | 5033 | 3887 |
| $AUC_u$ (nM · h) | 5.0 | 7.8 |

Note:
$AUC_u = AUC_{0\text{-}inf} \times$ Unbound PPB (Rat in vivo test PPB)

Conclusion: The free drug concentration of the compound of formula (I) in rat plasma is higher than that of the reference compound.

Experimental Example 4: In Vivo Study

OCI-LY10SCID mouse xenograft tumor model:

Experimental Method: Subcutaneous Xenograft Tumor Model in Mice with Human B-Cell Lymphoma Tumor cells in the logarithmic growth phase were collected and resuspended in IMDM basal medium. Matrigel was added to adjust the concentration of cells to 4×107/Ml. Under sterile conditions, SCID mice were inoculate with cell suspension subcutaneously on the right back at a concentration of $4\times10^6$/0.1 mL/mouse. When the animal tumor reached about 131.55-227.87 $mm^3$, the tumor-bearing mice were divided into 5 groups according to the size of the tumor volume, with 8 rats in each group. On the day of the experiment, the animals were given corresponding drugs according to the groups.

TABLE 14

Pharmacodynamic studies of test substances on human B-cell lymphoma OCI-LY10 cell SCID mouse xenografts

| Group | Animal number | With or without drug | Dosage (mg/kg) | Dosed Volume (mL/kg) | Drug concentration (mg/mL) | Route | Frequency |
|---|---|---|---|---|---|---|---|
| 1 | 8 | Vehicle | NA | NA | 10 | PO | QD × 21 |
| 2 | 8 | reference example | 45 | 4.5 | 10 | PO | QD × 21 |
| 3 | 8 | Form C | 15 | 1.5 | 10 | PO | QD × 21 |
| 4 | 8 | Form C | 30 | 3 | 10 | PO | QD × 21 |
| 5 | 8 | Form C | 45 | 4.5 | 10 | PO | QD × 21 |

Note:
PO means oral administration, QD means once a day.

During the experiment, the body weight and tumor size of the animals were measured 3 times a week, and the clinical symptoms of the animals were observed and recorded every day, and each administration was referred to the last weighed animal body weight.

The length (a) and width (b) of the tumor were measured with a digital vernier caliper, and tumor volume (Tumor volume, TV) was calculated according to the formula below:

$$TV = a \times b^2/2.$$

Figure 11:
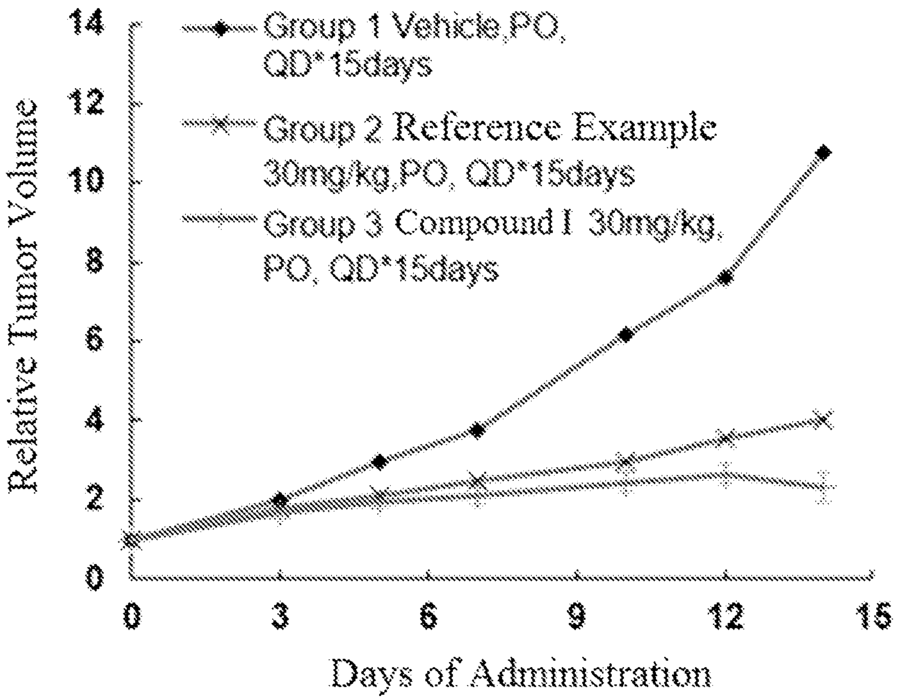
FIG. 11 is the tumor volume growth curve under the action of drugs.

Experimental results: See Table 15 for the evaluation of the antitumor efficacy of the test substance in the subcutaneous xenograft tumor model of human B-cell lymphoma OCI-LY10 cells. See FIG. 11 for the growth curve of the tumor volume under the action of the drug.

TABLE 15

Evaluation of the antitumor efficacy of the test substance in the subcutaneous xenograft model of human B-cell lymphoma OCI-LY10 cells (calculated based on the tumor volume on Day 20 after administration)

| Group | Tumor volume ($mm^3$)[a] (Day 0) | Tumor volume ($mm^3$)[a] (Day 20) | T/C[b] (%) | TGI[b] (%) |
|---|---|---|---|---|
| Vehicle | 181.29 ± 10.01 | 754.86 ± 27.75 | — | — |
| reference example 45 mg/kg | 183.86 ± 9.48 | 330.27 ± 19.35 | 42.45 | 74.47 |
| Form C 15 mg/kg | 182.02 ± 9.76 | 471.07 ± 16.55 | 65.50 | 49.61 |
| Form C 30 mg/kg | 180.91 ± 9.67 | 342.95 ± 20.06 | 45.05 | 71.75 |
| Form C 45 mg/kg | 180.19 ± 10.07 | 221.38 ± 37.11 | 29.25 | 92.82 |

Note:
[a]Mean ± SEM. Mean tumor volumes were calculated based on the animal's tumor volume at each measurement. Data points represent mean tumor volume change within groups and error bars represent standard error of mean (SEM);
[b]Tumor growth inhibition calculated by T/C and TGI.
— indicates no data.

Conclusion: In terms of drug efficacy in vivo in the human B-cell lymphoma OCI-LY10 cell subcutaneous xenograft tumor model, crystal form C could significantly inhibit tumor growth, whose inhibitory effect was positively correlated with dose. At the same dose, tumor inhibitory effect of crystal form C was obviously better than that of reference compound.

The invention claimed is:

1. A crystal form A of a compound of formula (I), wherein the X-ray powder diffraction pattern of the crystal form A comprises characteristic diffraction peaks at the 2θ angles of 16.16±0.20°, 16.60±0.20°, 22.02±0.20°, and 23.08±0.20°, (I)

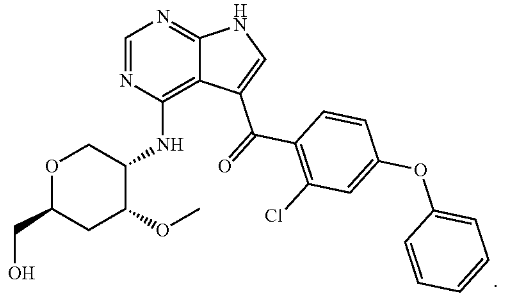

2. The crystal form A according to claim 1, wherein the X-ray powder diffraction pattern of the crystal form A comprises characteristic diffraction peaks at the 2θ angles of 7.51±0.20°, 10.63±0.20°, 15.06±0.20°, 16.16±0.20°, 16.60±0.20°, 21.28±0.20°, 22.02±0.20°, and 23.08±0.20°.

3. The crystal form A according to claim 2, wherein the X-ray powder diffraction pattern of the crystal form A comprises characteristic diffraction peaks at the 2θ angles of 7.51±0.20°, 10.63±0.20°, 12.00±0.20°, 13.17±0.20°, 15.06±0.20°, 16.16-0.20°, 16.60-0.20°, 18.61±0.20°, 21.28±0.20°, 22.02±0.20°, 22.49±0.20°, and 23.08±0.20°.

4. The crystal form A according to claim 3, wherein the X-ray powder diffraction pattern of the crystal form A comprises characteristic diffraction peaks at the 2θ angles of 7.51°, 9.45°, 10.04°, 10.63°, 12.00°, 13.17°, 14.25°, 15.06°, 15.51°, 16.16°, 16.60°, 17.31°, 17.58°, 18.61°, 18.95°, 19.53°, 20.07°, 20.60°, 21.28°, 21.78°, 22.02°, 22.49°, and 23.08°; or the X-ray powder diffraction pattern of the crystal form A is represented by FIG. 1.

Figure 2:
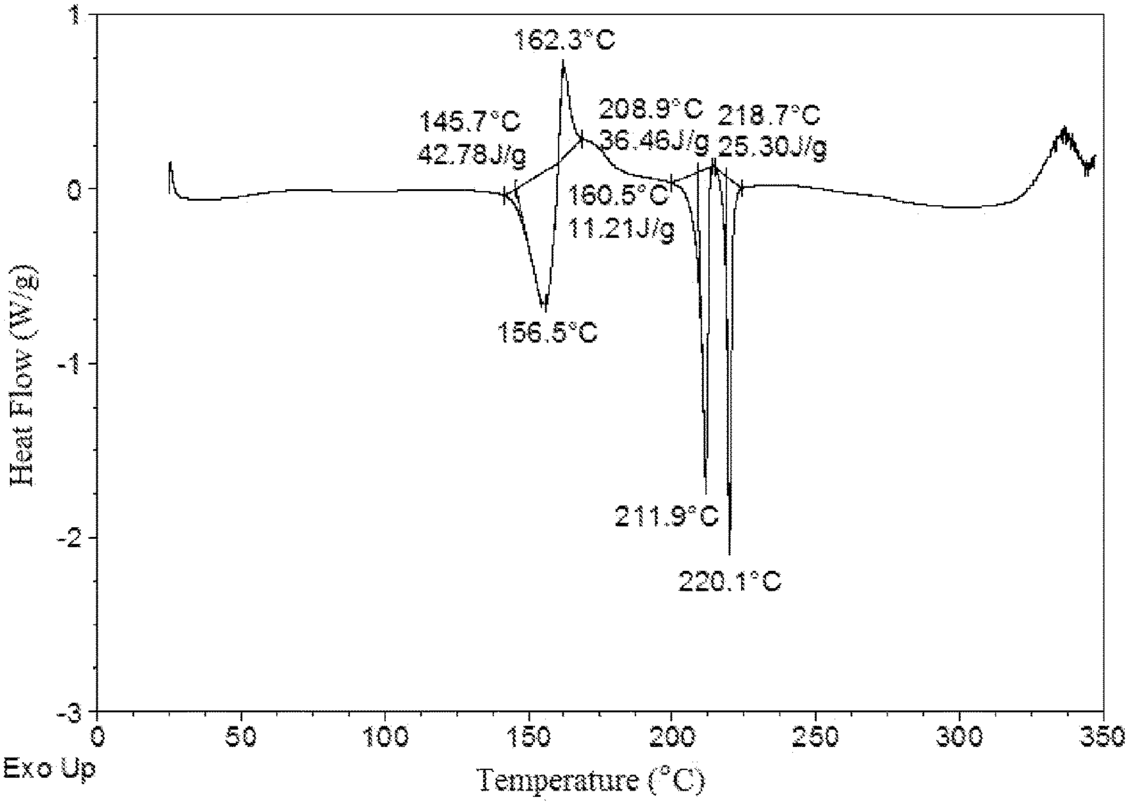
FIG. 2 is the DSC spectrogram of formula (I) compound crystal form A.
Figure 3:
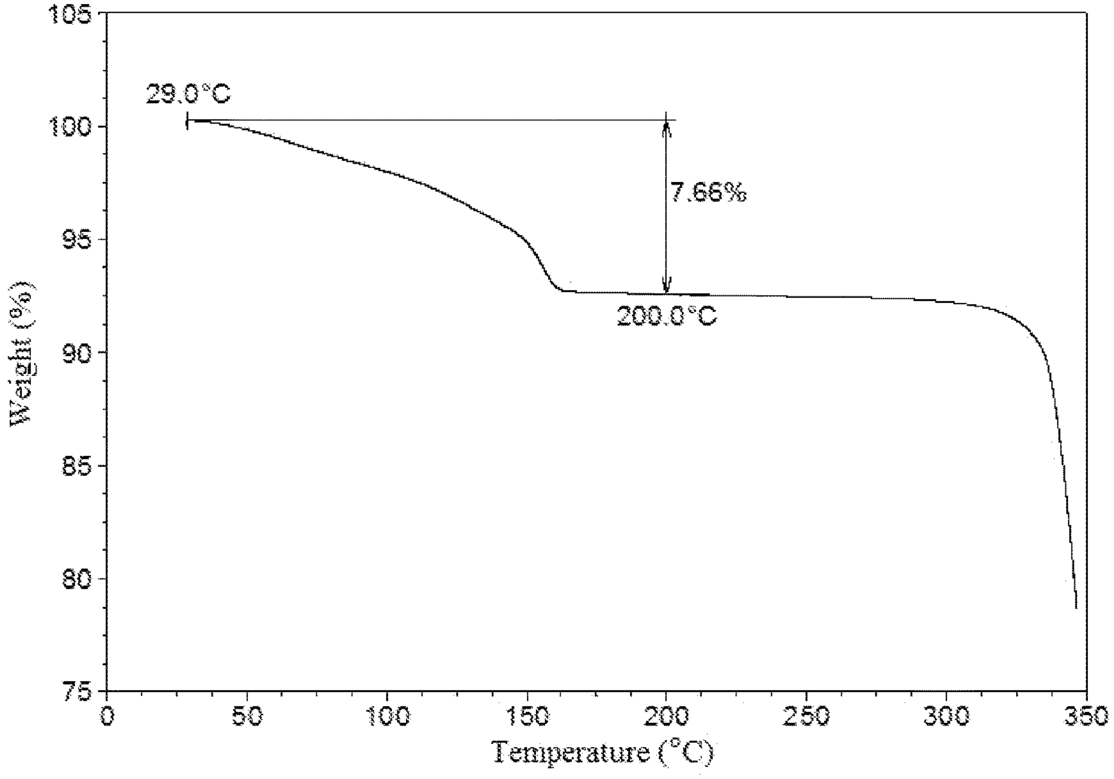
FIG. 3 is the TGA spectrogram of formula (I) compound crystal form A.

5. The crystal form A according to claim 1, wherein the differential scanning calorimetry spectrum of the crystal form A comprises endothermic peaks having onset values of 145.7° C.±3.0° C., 208.9° C.±3.0° C. and 218.7° C.±3.0° C., respectively, or the differential scanning calorimetry spectrum of the crystal form A is represented by FIG. 2; and/or the thermogravimetric analysis spectrum of the crystal form A has a weight loss of 7.66% at 200.0° C.±3.0° C., or the thermogravimetric analysis spectrum of the crystal form A is represented by FIG. 3.

6. A crystal form B of a compound of formula (I), wherein the X-ray powder diffraction pattern of the crystal form B comprises characteristic diffraction peaks at the 2θ angles of 7.47±0.20°, 10.41±0.20°, 16.04±0.20°, and 16.73±0.20°, (I)

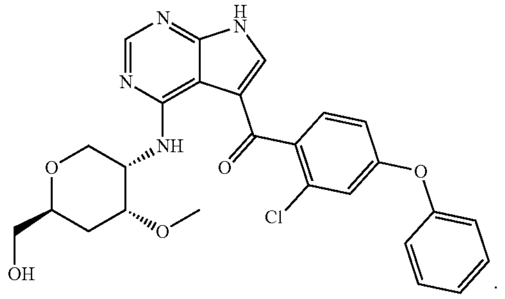

7. The crystal form B according to claim 6, wherein the X-ray powder diffraction pattern of the crystal form B comprises characteristic diffraction peaks at the 2θ angles of 7.47±0.20°, 10.41±0.20°, 15.23±0.20°, 16.04±0.20°, 16.73±0.20°, 20.87±0.20°, 21.46±0.20°, and 21.91±0.20°.

8. The crystal form B according to claim 7, wherein the X-ray powder diffraction pattern of the crystal form B comprises characteristic diffraction peaks at the 2θ angles of 7.47±0.20°, 9.53±0.20°, 10.41±0.20°, 11.91±0.20°, 13.91±0.20°, 15.23±0.20°, 16.04±0.20°, 16.73±0.20°, 18.82±0.20°, 20.87±0.20°, 21.46±0.20°, and 21.91±0.20°.

Figure 4:
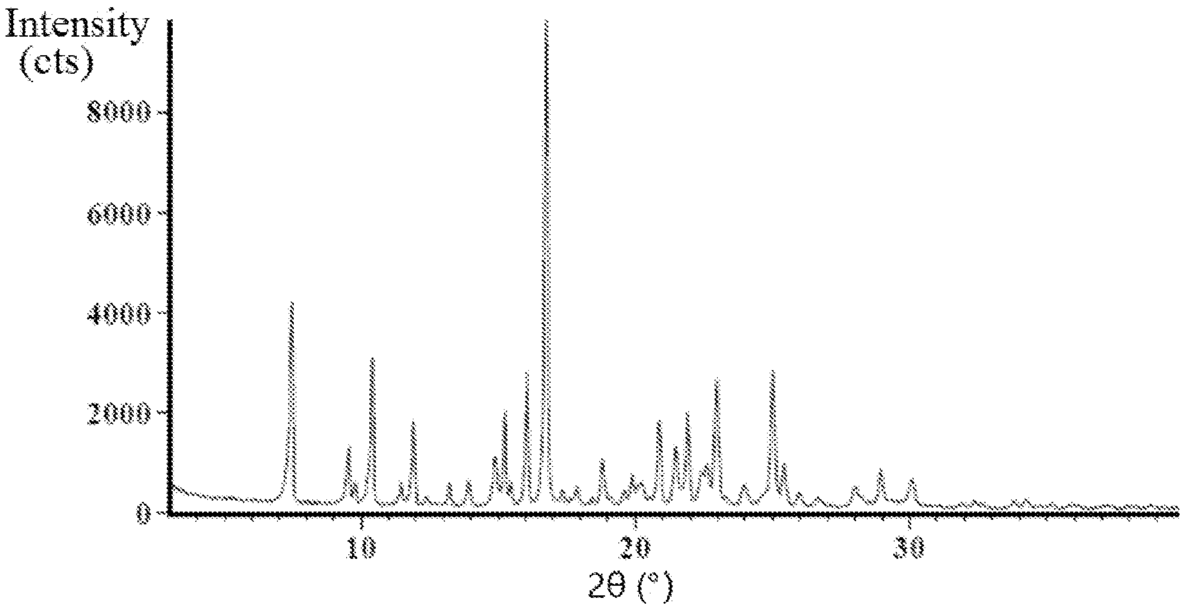
FIG. 4 is the Cu-Kα radiation XRPD spectrogram of formula (I) compound crystal form B.

9. The crystal form B according to claim 8, wherein the X-ray powder diffraction pattern of the crystal form B comprises characteristic diffraction peaks at the 2θ angles of 7.47°, 9.53°, 9.78°, 10.41°, 11.45°, 11.91°, 12.40°, 13.22°, 13.91°, 14.87°, 15.23°, 15.44°, 16.04°, 16.73°, 17.33°, 17.88°, 18.82°, 19.61°, 19.88°, 20.25°, 20.87°, 21.46°, and 21.91°, or the X-ray powder diffraction pattern of the crystal form B is represented by FIG. 4.

Figure 5:
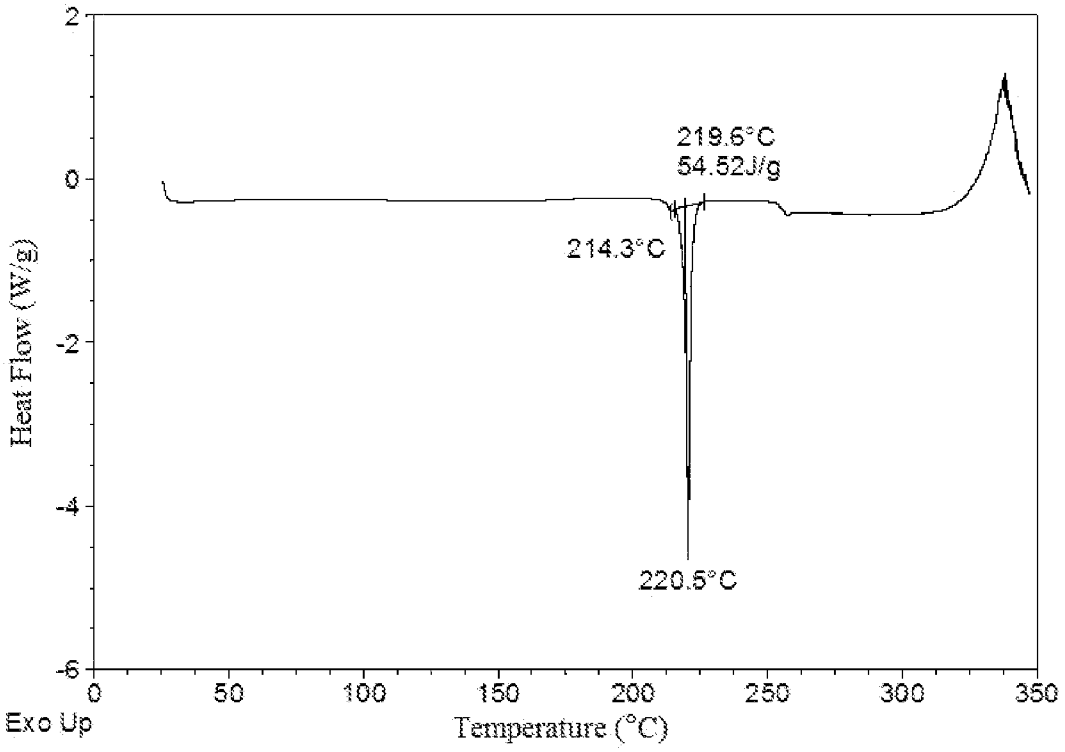
FIG. 5 is the DSC spectrogram of formula (I) compound crystal form B.
Figure 6:
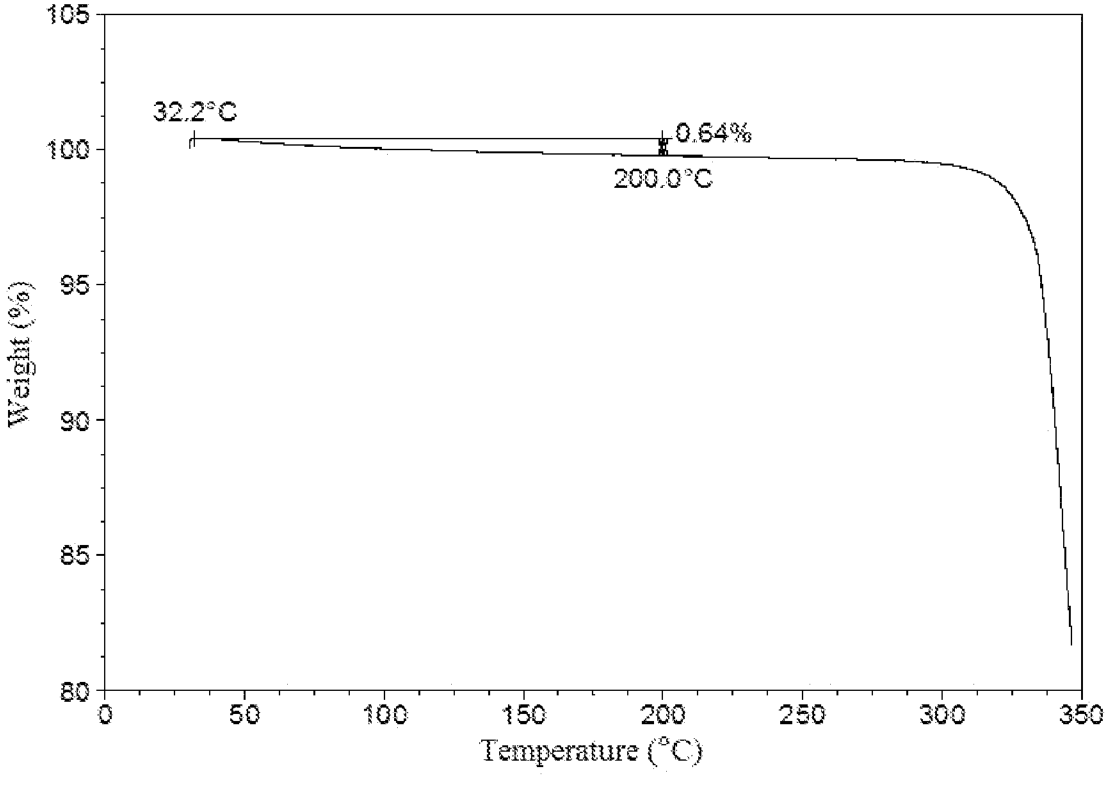
FIG. 6 is the TGA spectrogram of formula (I) compound crystal form B.

10. The crystal form B according to claim 6, wherein the differential scanning calorimetry spectrum of the crystal form B comprises an endothermic peak having an onset value of 214.3° C.±3.0° C., or the differential scanning calorimetry spectrum of the crystal form B is represented by FIG. 5; and/or the thermogravimetric analysis spectrum of the crystal form B has a weight loss of 0.64% at 200.0° C.±3.0° C., or the thermogravimetric analysis spectrum of the crystal form B is represented by FIG. 6.

11. A crystal form C of a compound of formula (I), wherein the X-ray powder diffraction pattern of the crystal form C comprises characteristic diffraction peaks at the 2θ angles of 5.28±0.20°, 8.58±0.20°, 20.56±0.20°, and 24.55±0.20°.

(I)

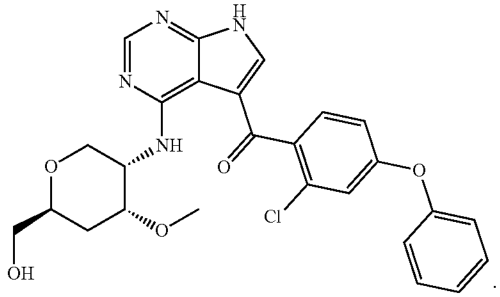

12. The crystal form C according to claim 11, wherein the X-ray powder diffraction pattern of the crystal form C comprises characteristic diffraction peaks at the 2θ angles of 5.28±0.20°, 8.58±0.20°, 11.00±0.20°, 11.52±0.20°, 15.72±0.20°, 20.56±0.20°, 21.84±0.20°, and 24.55±0.20°; or the X-ray powder diffraction pattern of the crystal form C comprises characteristic diffraction peaks at the 2θ angles of 5.28±0.20°, 8.58±0.20°, 11.00±0.20°, 11.52±0.20°, 15.72±0.20°, 16.69±0.20°, 17.16±0.20°, 18.62±0.20°, 19.76±0.20°, 20.56±0.20°, 21.84±0.20°, and 24.55±0.20°.

Figure 7:
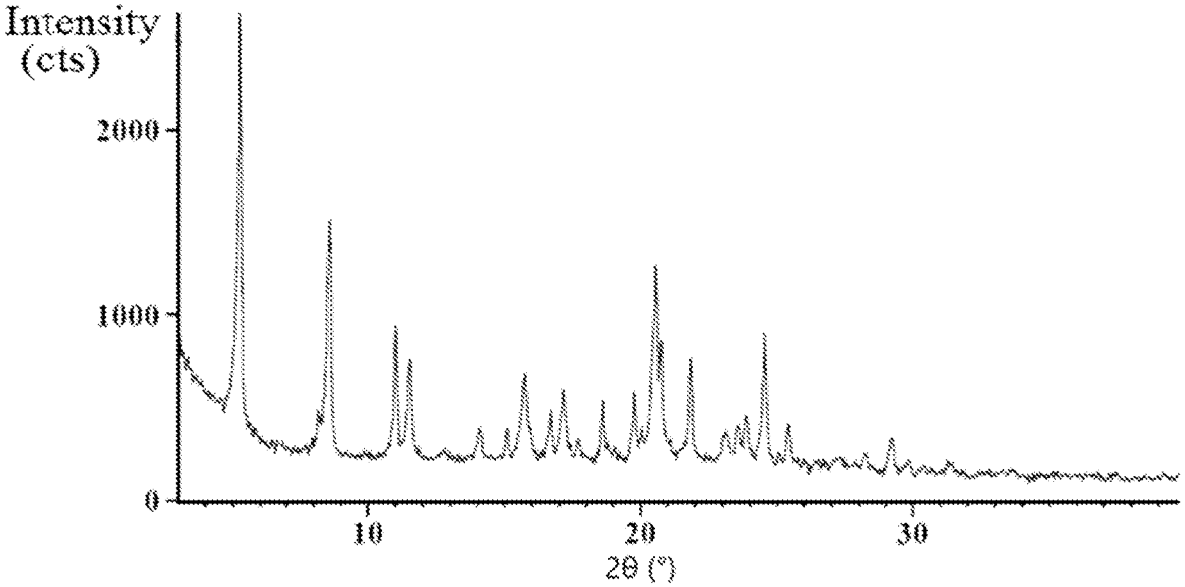
FIG. 7 is the Cu-Kα radiation XRPD spectrogram of formula (I) compound crystal form C.

13. The crystal form C according to claim 12, wherein the X-ray powder diffraction pattern of the crystal form C comprises characteristic diffraction peaks at the 2θ angles of 5.28°, 8.58°, 11.00°, 11.52°, 14.08°, 15.08°, 15.72°, 16.69°, 17.16°, 18.62°, 19.76°, 20.56°, 20.77°, 21.84°, 23.14°, 23.89°, 24.55°, 25.40°, 28.24°, 29.21°, and 31.36°, or the X-ray powder diffraction pattern of the crystal form C is represented by FIG. 7.

Figure 8:
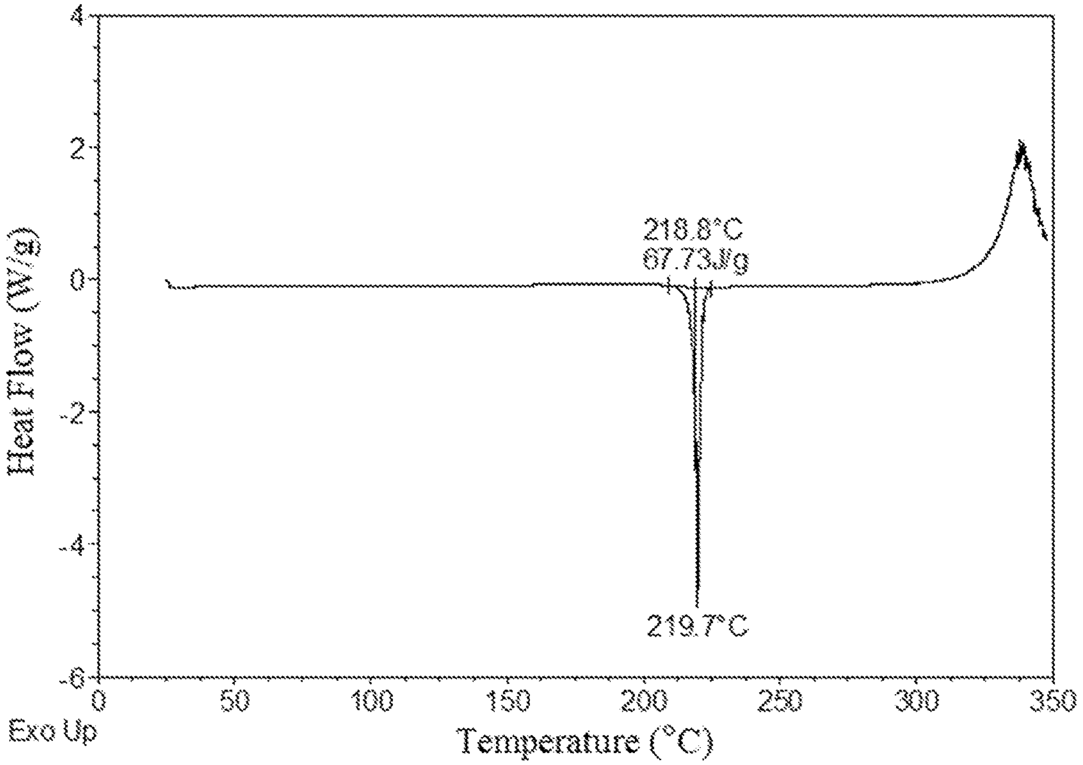
FIG. 8 is the DSC spectrogram of formula (I) compound crystal form C.
Figure 9:
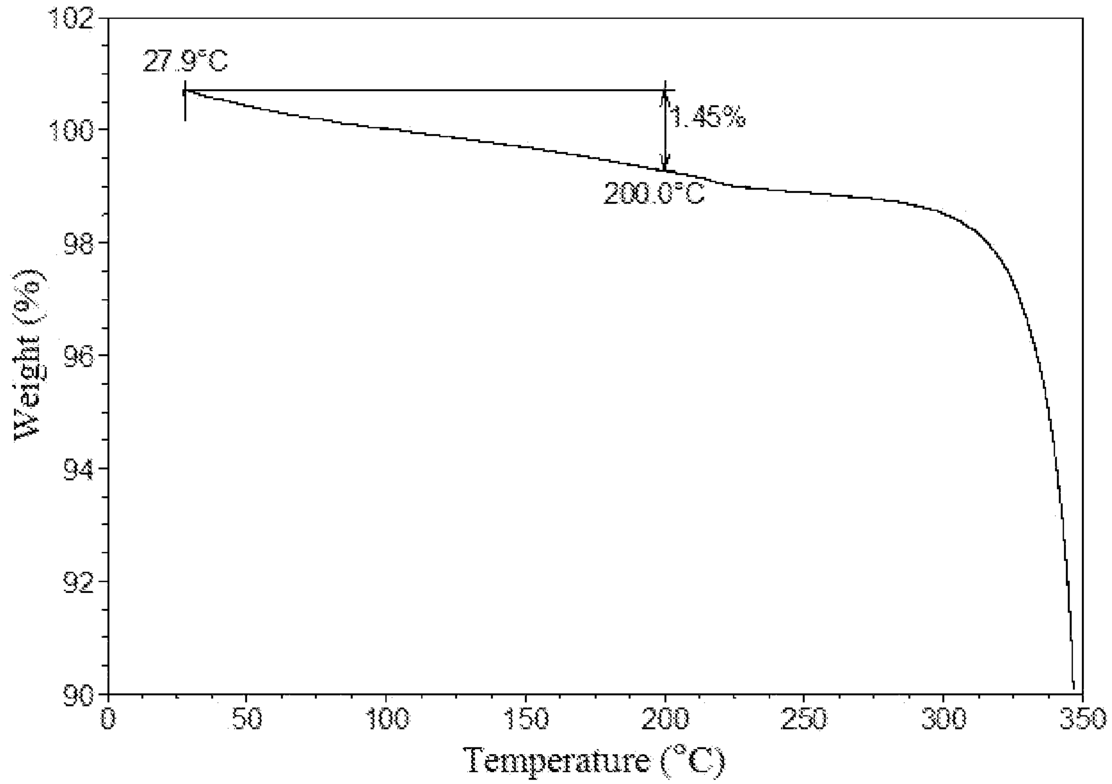
FIG. 9 is the TGA spectrogram of formula (I) compound crystal form C.

14. The crystal form C according to claim 11, wherein the differential scanning calorimetry spectrum of the crystal form C comprises an endothermic peak having an onset value of 218.8° C.±3.0° C., or the differential scanning calorimetry spectrum of the crystal form C is represented by FIG. 8; and/or the thermogravimetric analysis spectrum of the crystal form C has a weight loss of 1.45% at 200.0° C.±3.0° C., or the thermogravimetric analysis spectrum of the crystal form C is represented by FIG. 9.

15. A method for treating BTK protein kinase-related diseases, comprising administering the crystal form A according to claim 1 to a subject in need thereof, wherein the BTK protein kinase-related diseases are hematologic neoplasms.

16. A method for treating BTK protein kinase-related diseases, comprising administering the crystal form B according to claim 6 to a subject in need thereof, wherein the BTK protein kinase-related diseases are hematologic neoplasms.

17. A method for treating BTK protein kinase-related diseases, comprising administering the crystal form C according to claim 11 to a subject in need thereof, wherein the BTK protein kinase-related diseases are hematologic neoplasms.

* * * * *